(12) United States Patent
Wan

(10) Patent No.: US 12,178,459 B2
(45) Date of Patent: *Dec. 31, 2024

(54) SUCTION EVACUATION DEVICE

(71) Applicant: Shaw P. Wan, Norwood, NC (US)

(72) Inventor: Shaw P. Wan, Norwood, NC (US)

(73) Assignee: Well Lead Co, LTD, Guangzhou (CN)

( * ) Notice: Subject to any disclaimer, the term of this patent is extended or adjusted under 35 U.S.C. 154(b) by 940 days.

This patent is subject to a terminal disclaimer.

(21) Appl. No.: 17/036,965

(22) Filed: Sep. 29, 2020

(65) Prior Publication Data

US 2021/0022757 A1 Jan. 28, 2021

Related U.S. Application Data

(62) Division of application No. 14/341,905, filed on Jul. 28, 2014, now Pat. No. 10,828,051.

(51) Int. Cl.
*A61B 17/221* (2006.01)
*A61B 17/22* (2006.01)
*A61B 17/34* (2006.01)

(52) U.S. Cl.
CPC ............ *A61B 17/221* (2013.01); *A61B 17/22* (2013.01); *A61B 17/22012* (2013.01); *A61B 2017/22038* (2013.01); *A61B 2017/22074* (2013.01); *A61B 2017/22079* (2013.01); *A61B 2017/3445* (2013.01); *A61B 2217/005* (2013.01)

(58) Field of Classification Search
CPC ..... A61B 17/22; A61B 17/221; A61B 17/225; A61B 17/2251; A61B 17/22004–2017/22025; A61B 2017/22038; A61B 2017/22041; A61B 2017/22074; A61B 2017/22079; A61B 2017/3486; A61B 2017/2253; A61B 2217/005; A61M 1/06–068; A61M 1/0031–0035; A61M 1/0041; A61M 25/0041; A61M 25/0097; A61M 1/7411
See application file for complete search history.

(56) References Cited

U.S. PATENT DOCUMENTS 4,273,126 A * 6/1981 Grane ..................... A61M 1/74
433/92
4,583,970 A * 4/1986 Kirchner ................. A61M 1/06
604/184

(Continued)

*Primary Examiner* — Katherine H Schwiker
(74) *Attorney, Agent, or Firm* — Blake E. Vande Garde; AVEK IP, LLC

(57) ABSTRACT

A method for removing a stone from a patient comprising the steps of: providing a suction evacuation assembly which includes a sheath and one or more side arms; inserting and positioning a distal end of the sheath into a lumen or cavity of a patient's body containing a stones; connecting a tube to one of the side arms and to a collection bottle; connecting another tube to the collection bottle and a negative pressure system; visualizing the stone or foreign body using a scope inserted through the assembly; activating the negative pressure system in order to remove the stone from the cavity if the diameter of the stone is narrower than an inside diameter of the sheath and the side arm, or performing a lithotripsy on the stone to create fragments with a decreased diameter which allow the passage through the assembly; and collecting the stone in the collection bottle.

13 Claims, 11 Drawing Sheets

(56) References Cited

U.S. PATENT DOCUMENTS

| | | | | |
|---|---|---|---|---|
| 4,772,262 A | * | 9/1988 | Grant | A61M 1/06935 604/74 |
| 5,336,176 A | * | 8/1994 | Yoon | A61B 17/3417 604/164.11 |
| 5,358,472 A | * | 10/1994 | Vance | A61B 17/320758 606/159 |
| 5,419,769 A | * | 5/1995 | Devlin | A61M 1/76 604/326 |
| 5,584,803 A | * | 12/1996 | Stevens | A61M 25/0147 604/6.16 |
| 5,665,080 A | * | 9/1997 | Vandenberg | A61M 1/84 128/207.14 |
| 5,730,727 A | * | 3/1998 | Russo | A61M 1/7411 604/118 |
| 5,772,642 A | * | 6/1998 | Ciamacco, Jr. | A61N 5/1002 604/529 |
| 5,772,678 A | * | 6/1998 | Thomason | A61B 17/3417 604/164.1 |
| 5,830,224 A | * | 11/1998 | Cohn | A61B 17/11 606/167 |
| 5,921,970 A | * | 7/1999 | Vandenberg | A61M 1/84 604/275 |
| 5,971,938 A | * | 10/1999 | Hart | A61B 17/22031 606/127 |
| 6,017,493 A | * | 1/2000 | Cambron | A61M 1/3638 604/6.15 |
| 6,056,700 A | * | 5/2000 | Burney | A61B 90/39 604/63 |
| 6,093,168 A | * | 7/2000 | Mendenhall | A61M 1/062 604/74 |
| 6,159,195 A | * | 12/2000 | Ha | A61M 25/104 604/523 |
| 6,235,026 B1 | * | 5/2001 | Smith | A61B 17/32056 606/113 |
| 6,796,991 B2 | * | 9/2004 | Nardeo | A61M 25/0668 606/191 |
| 6,849,068 B1 | * | 2/2005 | Bagaoisan | A61M 25/0668 604/523 |
| 6,997,867 B2 | * | 2/2006 | Soble | A61B 1/307 600/156 |
| 2004/0267213 A1 | * | 12/2004 | Knapp | A61B 17/0218 604/284 |
| 2005/0228410 A1 | * | 10/2005 | Berreklouw | A61F 2/2448 606/153 |
| 2005/0240165 A1 | * | 10/2005 | Miki | A61M 25/0068 604/528 |
| 2009/0216246 A1 | * | 8/2009 | Nita | A61B 17/22004 606/128 |
| 2009/0270896 A1 | * | 10/2009 | Sullivan | A61B 17/00234 606/170 |
| 2011/0071539 A1 | * | 3/2011 | LeVert | A61B 17/221 606/113 |
| 2011/0152823 A1 | * | 6/2011 | Mohiuddin | A61B 17/221 604/500 |
| 2015/0011827 A1 | * | 1/2015 | Kinoshita | A61B 1/00154 600/114 |
| 2017/0086939 A1 | * | 3/2017 | Vayser | A61B 1/07 |

* cited by examiner

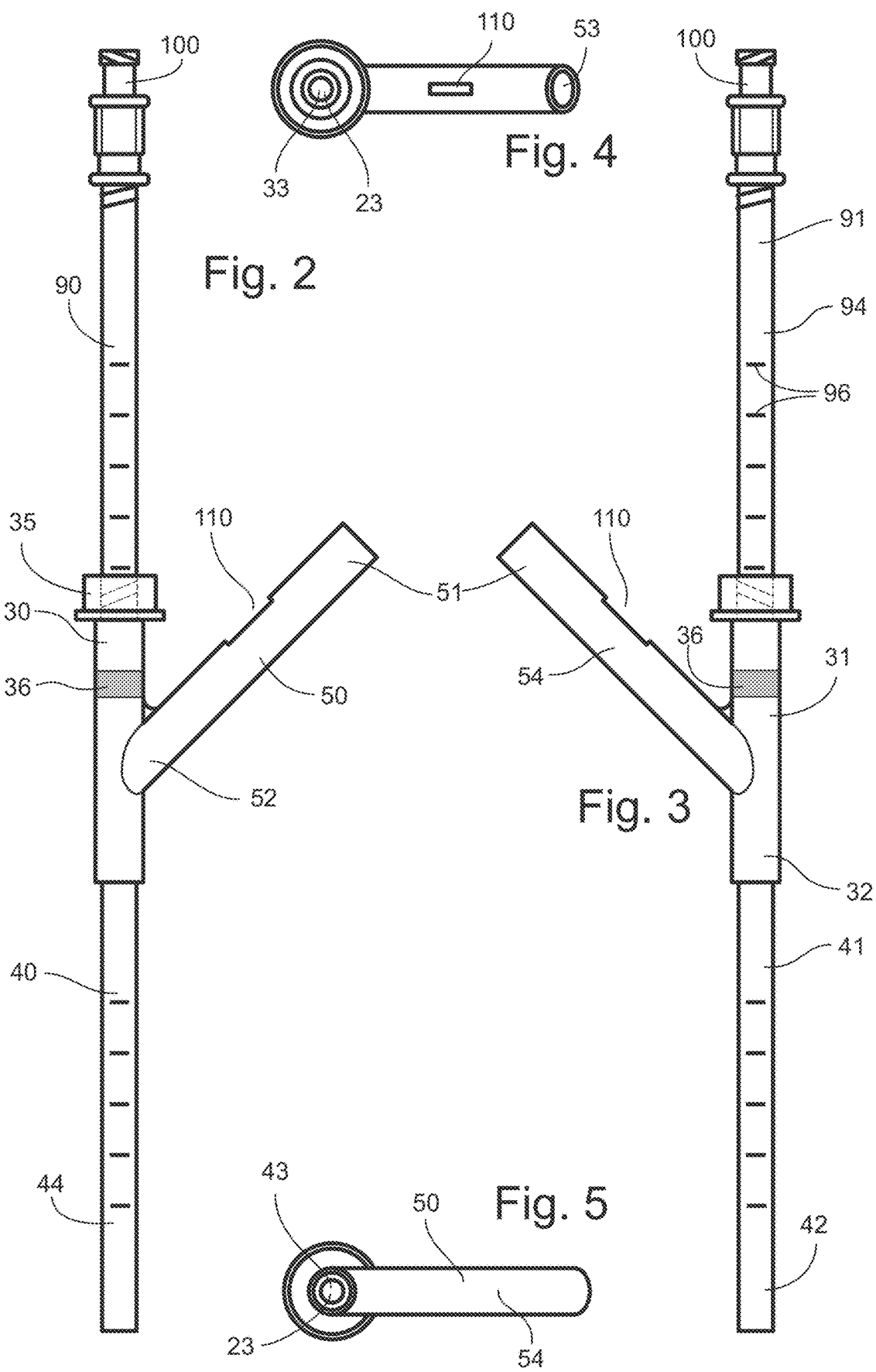

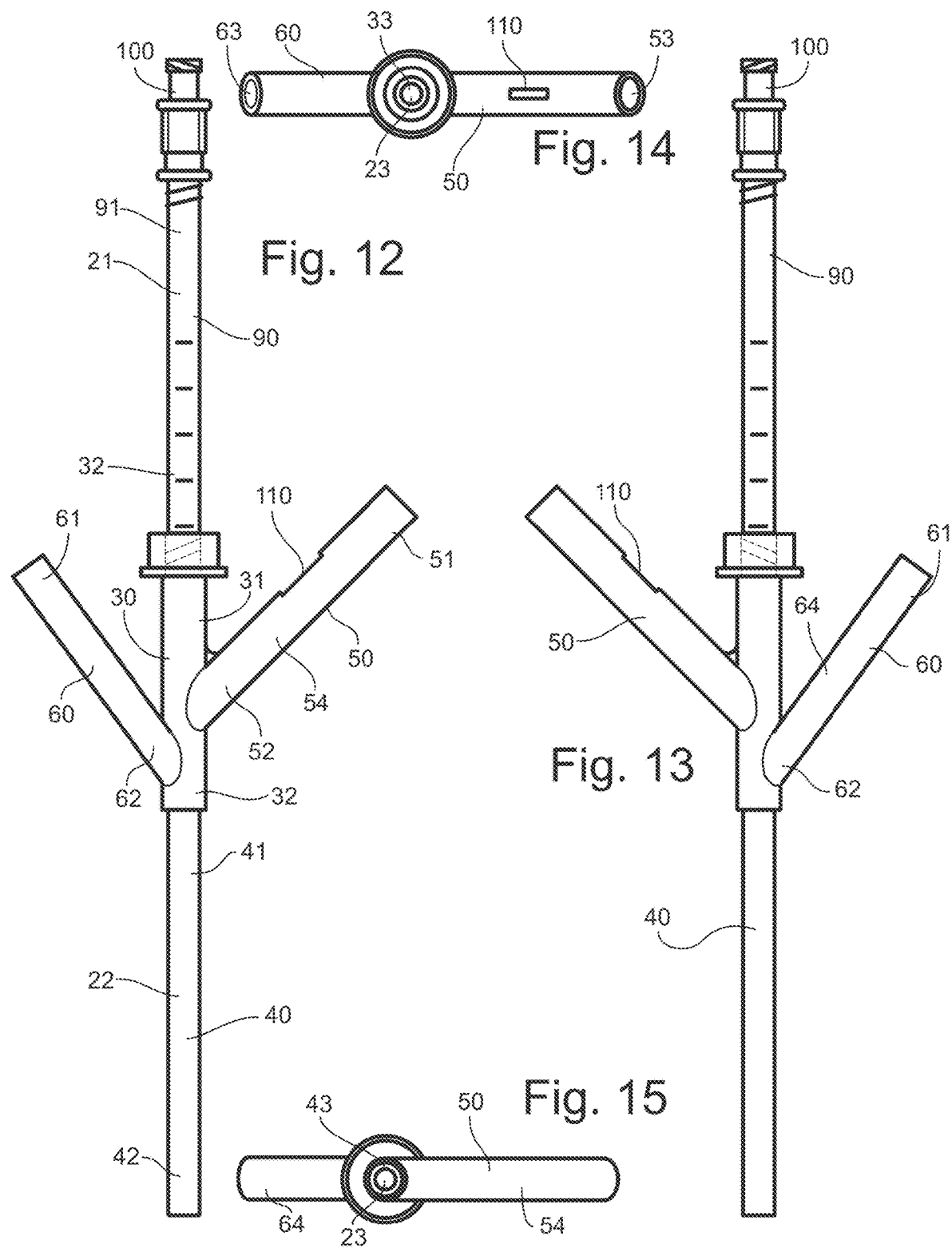

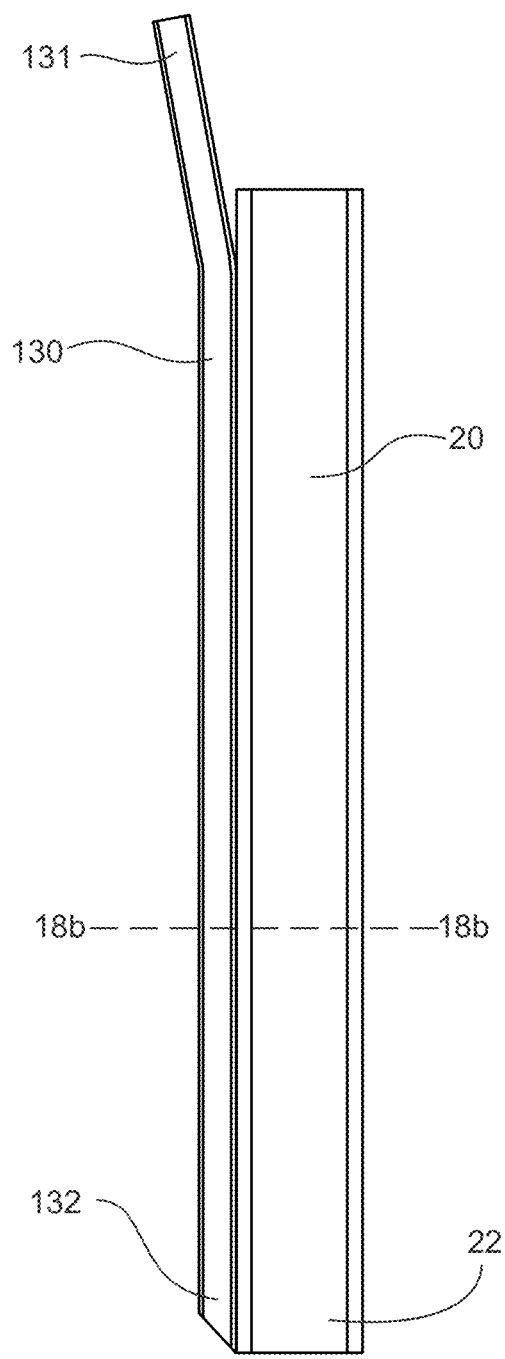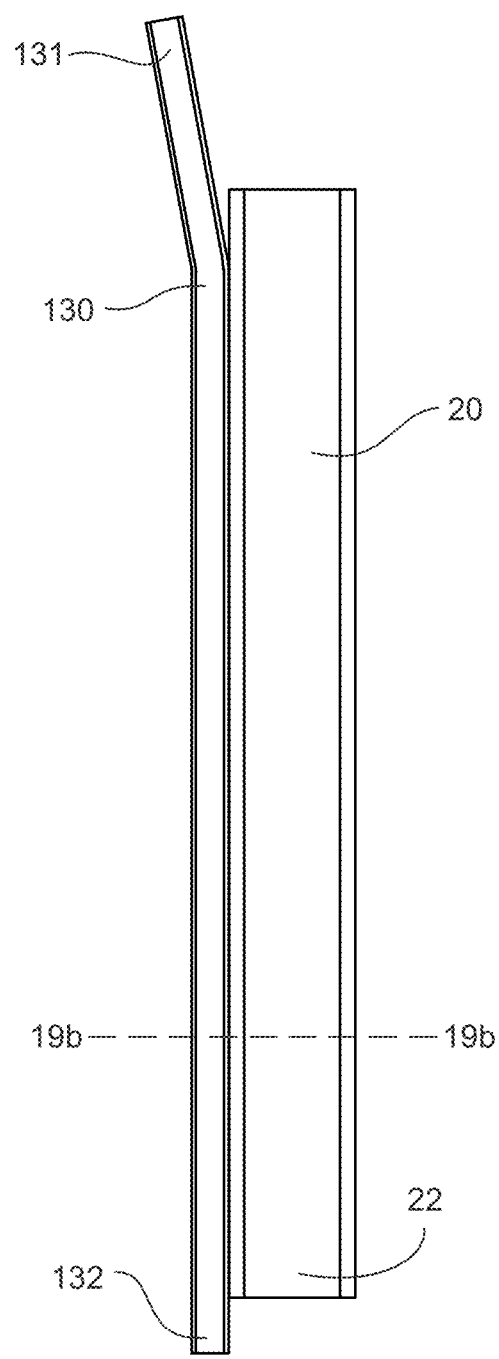
Fig. 18a Fig. 19a
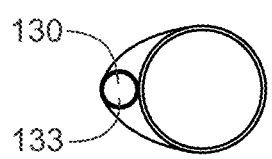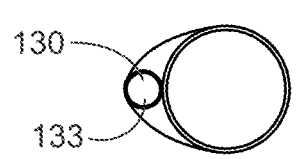
Fig. 18b Fig. 19b

SUCTION EVACUATION DEVICE

RELATED CASES

This is a divisional application of U.S. patent application Ser. No. 14/341,905 filed on Jul. 28, 2014. The full disclosure of that application is expressly incorporated herein by reference.

FIELD OF THE INVENTION

A surgical device used to retrieve stones from a patient's body is disclosed herein below.

BACKGROUND OF THE INVENTION

Kidney stones and gallstones have plagued mankind for ages. Complications resulting from the presence of stones in the urinary tract or biliary tract often require surgical intervention to remedy the problem. A patient will require several days in the hospital to recover from a typical surgical procedure to remove a stone wherein a surgeon incises a patient's abdomen in order to remove the stone. The use of less invasive stone retrieval devises has decreased the suffering and recovery time required by a patient.

During the past 40 years great strides have been made in the treatment of stone disease, especially in the field of extracorporeal and endoscopic lithotripsy. However, all the inventions focus on the access and fragmentation of the stones. Extracorporeal shock wave lithotripsy uses pressure waves to crush the stone, but then requires the patient to pass the stone fragments on their own. Amplatz percutaneous nephrostomy sheaths and various ureteral sheaths allow access to the stones for lithotripsy. However, they require either the patient to pass the stone fragments on their own or to have the stone removed at the time of lithotripsy using pressure irrigation and/or stone forceps. Pressure irrigation and stone forceps tend to increase operative time as well as surgical complications.

While the stone retrieval devices known in the prior art performed adequately, there is significant room for improvement. The stone retrieval device disclosed below is an improvement over those known in the art.

SUMMARY OF THE INVENTION

A method for removing a stone from a patient comprising the steps of: providing a suction evacuation assembly which includes a sheath and one or more side arms; inserting and positioning a distal end of the sheath into a lumen or cavity of a patient's body containing a stones; connecting a tube to one of the side arms and to a collection bottle; connecting another tube to the collection bottle and a negative pressure system; visualizing the stone or foreign body using a scope inserted through the assembly; activating the negative pressure system in order to remove the stone from the cavity if the diameter of the stone is narrower than an inside diameter of the sheath and the side arm, or performing a lithotripsy on the stone to create fragments with a decreased diameter which allow the passage through the assembly; and collecting the stone in the collection bottle. The irrigation is generally provided through the endoscope; however, additional irrigation can be added through the secondary side arm or arms.

Whereas this device was initially developed for the treatment of stone disease; using the same principle, it soon becomes apparent that this device is also applicable for the removal of a foreign body in the body cavity or lumen and can be used for tissue ablation.

DESCRIPTION OF THE DRAWINGS

For the purpose of illustrating the invention, there is shown in the drawings a form that is presently preferred; it being understood, however, that this invention is not limited to the precise arrangements and instrumentalities shown.

FIG. 2 is a front view of one embodiment of the present invention.

FIG. 3 is a back view of one embodiment of the present invention.

FIG. 4 is a top-down view of one embodiment of the present invention.

FIG. 5 is a bottom-up view of one embodiment of the present invention.

FIG. 12 is a front view of one embodiment of the present invention.

FIG. 13 is a back view of one embodiment of the present invention.

FIG. 14 is a top-down view of one embodiment of the present invention.

FIG. 15 is a bottom-up view of one embodiment of the present invention.

FIG. 18a is a side view of one embodiment of the present invention.

FIG. 18b is a cut-through view of one embodiment of the present invention.

FIG. 19a is a side view of one embodiment of the present invention.

FIG. 19b is a cut-through view of one embodiment of the present invention.

DESCRIPTION OF THE INVENTION

Figure 16:
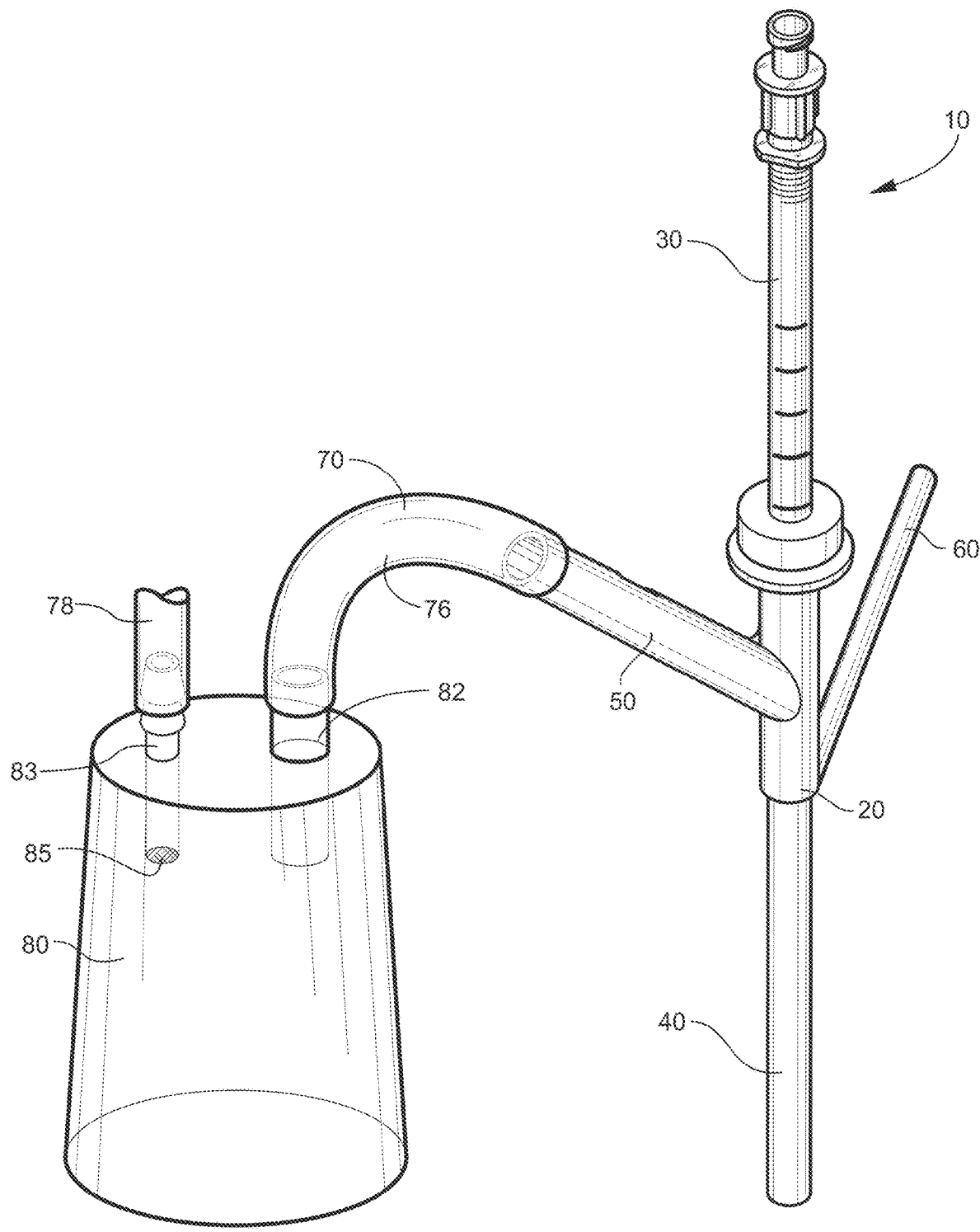
FIG. 16 is a perspective view of one embodiment of the present invention.

The current invention addresses numerous issues with the prior art and includes access to the stone in addition to providing a means for the removal of the stone fragments through negative pressure suction. Referring to the figures, where like numerals refer to like elements, there is shown a sheath 20 of the suction evacuation assembly 10 is to be used for endoscopic lithotripsy and extraction of stone fragments. One important feature of the current invention is a sheath 20 that has a side arm 50 that has an identical or nearly identical luminal circumference. The side arm 50 is connected a collection container 80 which is connected to a negative pressure aspirator 120 (see FIGS. 10 and 16). When stone fragments are smaller they can be evacuated through the sheath 20 in the space between the endoscope and the sheath 20. When the stone fragments are larger, but still small enough to enter the sheath lumen 23, the endoscope can be withdrawn to a location that is just proximal to the distal end 52 of the side arm 50. This location is marked by a colored band that can be seen both externally and internally (through the scope). With the scope in this position, the sheath 20 and the side arm lumens now have a similar caliber channel with the side port channel equal or slightly larger than the sheath channel. The stone fragments or foreign body have an unimpeded evacuation route. This allows a continuous evacuation channel for the stone fragments to reach the collection container 80. During the development of the device disclosed in the instant invention, it was found that the device could also be used to remove a foreign body from a patient's body cavity or lumen. Additionally, the device could also be used for tissue ablation and morcellation.

The present invention involves a method of using a suction evacuation assembly 10 for removing one or more stones or foreign bodies from within a patient. The suction evacuation assembly includes a sheath 20, an obturator 90, a flexible cap 100, connecting tubing 70, and collection container 80. More specifically, the present invention discloses a method for removing a stone, a stone fragment or a foreign body from a patient using a suction evacuation assembly 10 comprising the steps of:

(a) providing a suction evacuation assembly 10 which includes a sheath 20 and one or more side arms 50;
(b) inserting an obturator 90 into a proximal end 21 of a sheath 20 and securing the obturator to the proximal end of the sheath the sheath being comprised of a proximal sheath 30 and a distal sheath 40, wherein the proximal sheath 30 has a proximal end 31 and a distal end 32 and the distal sheath 40 has a proximal end 41 and a distal end 42, wherein the distal end 32 of the proximal sheath 30 is secured to the proximal end 41 of the distal sheath 40 and wherein the proximal sheath 30 has one or more side arms 50 emanating from the outer surface 34 of the proximal sheath, and wherein the sheath 20 has a lumen 23 which is the same diameter as a lumen 53 of the one or more side arms 50;
(c) inserting a distal end 22 of the sheath into a lumen or cavity of a patient's body containing one or more stones or foreign bodies;
(d) positioning the distal end to of the sheath in a position in close proximity to the stones or foreign bodies;
(e) disengaging the obturator 90 from the proximal end 21 of the sheath and removing the obturator from the sheath 20;
(f) securing a flexible cap 100 to the proximal end of the sheath;
(g) connecting one end of a primary tube 76 to one of the side arms 50 and connecting the other end of the primary tube 76 to a collection container 80;
(h) connecting one end of a secondary tube 78 to the collection container 80 and connecting the other end of the secondary tube 78 to a negative pressure system 120;
(i) inserting a scope into the sheath through the flexible cap and into the patient;
(j) visualizing the stone or foreign body using the scope;
(k) activating the negative pressure system 120 in order to remove the stone or foreign body from the cavity if a diameter of the stone or foreign body is narrower than an inside diameter of the sheath lumen 23 and the inside diameter of the side arm lumen 53, or
(l) performing a lithotripsy on the stone or the foreign body in order to create fragments with a decreased diameter which allow the passage of the fragments between the endoscope and sheath lumen 23 or within the inside diameter of the sheath lumen 23 and the inside diameter of the side arm lumen 53 when the endoscope is withdrawn to the bifurcation (the color band 36); and
(m) collecting the stone, foreign body and/or fragments in the collection container 80.

Methodology for Tissue Ablation and Morcellation

The present invention also involves a method of using a suction evacuation assembly 10 for ablation and morcellation of tissue within a patient. The suction evacuation assembly includes a sheath 20, an obturator 90, a flexible cap 100, connecting tubing 70, and collection container 80. More specifically, the present invention discloses a method for ablation and morcellation from a patient using a suction evacuation assembly 10 comprising the steps of:

(a) providing a suction evacuation assembly 10 which includes a sheath 20 and one or more side arms 50;
(b) inserting an obturator 90 into a proximal end 21 of a sheath 20 and securing the obturator to the proximal end of the sheath the sheath being comprised of a proximal sheath 30 and a distal sheath 40, wherein the proximal sheath 30 has a proximal end 31 and a distal end 32 and the distal sheath 40 has a proximal end 41 and a distal end 42, wherein the distal end 32 of the proximal sheath 30 is secured to the proximal end 41 of the distal sheath 40 and wherein the proximal sheath 30 has one or more side arms 50 emanating from the outer surface 34 of the proximal sheath, and wherein the sheath 20 has a lumen 23 which is the same diameter as a lumen 53 of the one or more side arms 50;
(c) inserting a distal end 22 of the sheath 20 into a lumen or cavity of a patient's body containing the target tissue or organ;
(d) positioning the distal end to of the sheath in a position in close proximity to the tissue or organ;
(e) disengaging the obturator 90 from the proximal end 21 of the sheath and removing the obturator from the sheath 20;
(f) securing a flexible cap 100 to the proximal end of the sheath;
(g) connecting one end of a primary tube 76 to one of the side arms 50 and connecting the other end of the primary tube 76 to a collection container 80;
(h) connecting one end of a secondary tube 78 to the collection container 80 and connecting the other end of the secondary tube 78 to a negative pressure system 120;
(i) inserting a scope into the sheath through the flexible cap and into the patient;
(j) visualizing the target tissue or organ using the scope;
(k) activating the negative pressure system 120 in order to remove the tissue fragments.
(l) performing tissue ablation using thermal energy or morcellation of tissue using mechanical or thermal energy in order to create fragments with a decreased diameter which allow the passage of the fragments between the endoscope and sheath lumen 23 or within the inside diameter of the sheath lumen 23 and the inside diameter of the side arm lumen 53 when the endoscope is withdrawn to the bifurcation (the color band 36); and
(m) collecting tissue fragments in the collection container 80.

Irrigation is normally provided through the endoscope during the above process, however, additional irrigation can be added through the secondary side arm 60 or arms.

Sheath 20, as used herein, refers to a rigid, semi-rigid, or flexible tube. The sheath 20 can be constructed from any medical grade material including, but not limited to, nylon, polyethylene, polyvinyl chloride, polycarbonate, polypropylene, or fluorinated ethylene propylene. The sheath 20 may be reinforced with a rigid or a semi-rigid coil or filaments within its wall to add additional rigidity if desired. In one embodiment of the present invention, the sheath 20 is reinforced with radiopaque material. In another embodiment of the present invention, the sheath 20 may further include one or more radiopaque materials. The sheath 20 has a proximal end 21 through which instruments may be inserted and withdrawn. The sheath 20 has a distal end 22 which is inserted into a patient. The sheath 20 also has a lumen 23 and an outer surface 24. In one embodiment of the present invention, illustrated in FIGS. 1-10, the sheath 20 is comprised of a proximal sheath 30 and a distal sheath 40 in respect to the operator holding the device. The two sheaths (i.e., a proximal sheath and a distal sheath) can be joined together as a single piece or can be joined together in a sleeve type connection. The length of the sheath 20 may correspond to any length known in the art. In one embodiment, the length of the sheath is in the range of 15 to 45 cm. The lumen 23 of the sheath may be any diameter permits the passage of a scope which is commonly used in Lithotripsy. In one embodiment, the lumen may have a diameter in the range of 3 to 8 mm or 8 to 24 French. The sheath 20 may include markings on the outer surface 24 of the sheath which may aid in determining the position of the sheath within a patient based on distance. A radio-opaque material may also be used on the outer surface 24 of the sheath to aid in determining the position of the sheath within a patient. In one embodiment of the present invention, the distal end 22 of sheath 20 is made of expandable material. Once the distal end is inserted into a patient's body cavity or lumen it can be expanded by an expansion balloon, an expansion spring, or some another mechanism. The expanded distal end 22 can then be used to entrap the stone, foreign body, tissue or targeted organ inside sheath for treatment. In yet another embodiment, the distal end 22 of sheath 20 is constructed in a tapered configuration to facilitate the insertion of the said sheath into the patient's body cavity and lumen. Once the distal end 22 of sheath 20 is in place, the distal end 22 can then be expanded as needed.

The proximal sheath 30 has a proximal end 31 and a distal end 32. The proximal sheath 30 also includes a lumen 33 through which tools, instruments, stones and foreign bodies pass and an outer surface 34. The proximal sheath 30 is transparent or semi-transparent so that the stone fragments can be visualized as they travel up the lumen 33 and exit the side arm 50. The proximal sheath 30 has a connection fitting to receive a flexible cap 100. One embodiment of the present invention uses a hat like connecting joint. The proximal sheath 30 also has a connection mechanism 35 that allows for a secure connection between the proximal sheath 30 and the obturator 90. This connection will prevent separation of obturator 90 from the proximal sheath 30 during the insertion into a patient's body luminal cavity. This connection can be constructed in various shapes or types and includes a simple male to female screw-on connection. In one embodiment of the present invention, the female end of the connection is on the proximal end 31 of the proximal sheath 30. The length of the proximal sheath 30 may be in the range of 4 to 8 cm. The outer surface 34 of the proximal sheath 30 has one or more side arms 50, at least one of which is the accessory side arm 60.

The side arm 50 emanates up from the outer surface 34 of the proximal sheath 30 and forms an angle with the proximal sheath 30 in the range of >0° to <180°, between 10° and 170°, between 20° and 160°, between 30° and 150°, between 20° and 110°, between 20° and 90°, or between 20° and 70°. In one embodiment, the angle is 45° toward the proximal end 31 of the proximal sheath 30. In another embodiment, the angle is 30° toward the proximal end 31 of the proximal sheath 30. In still another embodiment, the angle is 25° toward the proximal end 31 of the proximal sheath 30. In one embodiment, the diameter of the lumen 53 of the side arm 50 is up to 20% smaller than the diameter of the lumen 33, 43 of the proximal 30 and the distal sheath 40. In another embodiment, the diameter of the lumen 53 of the side arm 50 has a diameter which is the same or up to 20% larger than the diameter of the lumen 33, 43 of the proximal 30 and the distal sheath 40. In yet another embodiment, the diameter of the lumen 53 of the side arm 50 is the same or larger than the diameter of the lumen of the sheath 23, 33, 43 to facilitate the efficient evacuation of stones, stone fragments or other foreign bodies. Each side arm 50 includes a proximal end 51 and a distal end 52 with the distal end 52 being secured to the outer surface 34 of the proximal sheath 30. The side arm 50 may also include a pressure regulating mechanism 110. The pressure regulating mechanism 110 may simply be a control vent in the form of a slit or a hole, or it may be a more elaborate mechanism such as a valve. In one embodiment of the present invention, a side arm 50 has a pressure regulating mechanism 110 in the form of a longitudinal slit in respect to the axis of the side arm 50 and acts as a control vent. When minimum negative pressure is required, the slit is left open or minimally occluded. When more negative pressure is required the slit is further occluded as needed to a maximum of complete closure. In another embodiment the pressure regulating mechanism 110 is placed on the egress tubing (connecting to the negative pressure system 120) in the form of a three way valve. Additionally, the egress tubing has two perpendicular sluices; the second sluice can be used to clear blood clots, tissue fragments, or stone fragments that might have been aspirated into the egress tubing and cause blockage. In another embodiment, a rubber or silicone seal is attached to the side arm 50. This seal can be used to close the control vent and relieve the operator from the burden of manually closing the control vent. In yet another embodiment, a push-pull mechanism is employed to close and open the control vent instead of having the operator manually close the control vent. Furthermore, the pressure regulating mechanism 110 can be placed anywhere along the egress path (i.e. the side arm 50, the connecting tubing 70, the collection container 80 or even on the aspirator (negative pressure system).

The proximal end 51 of the side arm 50 is configured to accept a connection to a flexible tubing 70. The proximal end 51 can be straight, flared, tapered, expandable, and/or ribbed and/or have a luer lock or some other type connector which may be used in conjunction with a variety of medical instruments known in the art which include, but are not limited to, a wire basket retriever, a guide wire, a stylet, a loop, a grasper, or the like. A backflow preventer may also be associated with the proximal end 51 of the accessory side arm. In one embodiment, the proximal end 51 is straight to avoid compromising the lumen 53 of the side arm 50 and thus reduce the efficiency of stone removal. In another embodiment, a marking is placed just proximal to the connection of the side arm 50 and the outer surface 34 of the proximal sheath 30. This marking can be seen both endoscopically and/or externally. The marking may be any color or material which may be easily visualized by the user of the suction evacuation assembly 10. In one embodiment, the side arm 50 further comprises a pressure regulating mechanism 110 which allows a person using the suction evacuation assembly 10 and to increase or decrease the negative pressure within the suction evacuation assembly.

In one embodiment of the present invention the proximal 30 and distal sheath 40 can be separated from one another. The distal sheath 40 is constructed with a peelable (tearable) material. This can also be achieved with a fabricated perforation along the longitudinal axis of the distal sheath 40. In a preferred embodiment, there are two lateral wings placed at the proximal ends of the distal sheath 40. This will facilitate the separation (peeling, tearing). In another embodiment the distal sheath 40 can be expanded. This can be achieved with an expansion balloon, an expansion spring, or some other mechanical means. The expansion can achieve two effects:

(1) Dilate the space where the distal sheath 40 traverses, and (2) Entrap the target within the distal sheath 40 for fragmentation, morcellation, ablation, or extraction.

In one embodiment of the present invention, the proximal sheath 30 has a second side arm (sluice) which is an accessory side arm 60. The accessory side arm 60 is generally used for additional irrigation or passage of a guide wire, stone basket or any other devices which may be needed during a foreign body removal procedure. It may also be used as an additional channel for the stone or foreign body evacuation. The second side arm may be located anywhere on the outer surface 34 of the proximal sheath. The accessory side arm 60 emanates up from the outer surface 34 of the proximal sheath 30 and forms an angle with the proximal sheath 30 in the range of >0° to <180°, between 10° and 170°, between 20° and 160°, between 30° and 150°, between 20° and 110°, between 20° and 90°, or between 20° and 70°. In one embodiment, the angle is 45° toward the proximal end 31 of the proximal sheath 30. In another embodiment, the angle is 30° toward the proximal end 31 of the proximal sheath 30. In still another embodiment, the angle is 25° toward the proximal end 31 of the proximal sheath 30. In one embodiment, the diameter of the lumen 63 of the accessory side arm 60 is up to 20% smaller than the diameter of the lumen 33, 43 of the proximal 30 and the distal sheath 40. In another embodiment, the diameter of the lumen 63 of the accessory side arm 60 has a diameter which is the same or up to 20% larger than the diameter of the lumen 33, 43 of the proximal 30 and the distal sheath 40. In yet another embodiment, the diameter of the lumen 63 of the accessory side arm 60 is the same or larger than the diameter of the lumen of the sheath 23, 33, 43 to facilitate the efficient evacuation of stones, stone fragments or other foreign bodies. Each accessory side arm 60 includes a proximal end 61 and a distal end 62 with the distal end 62 being secured to the outer surface 34 of the proximal sheath 30. The accessory side arm 60 may also include a pressure regulating mechanism 110. The pressure regulating mechanism 110 may simply be a control vent in the form of a slit or a hole, or it may be a more elaborate mechanism such as a valve. In one embodiment of the present invention, an accessory side arm 60 has a pressure regulating mechanism 110 in the form of a longitudinal slit in respect to the axis of the accessory side arm 60 and acts as a control vent. When minimum negative pressure is required, the slit is left open or minimally occluded. When more negative pressure is required the slit is further occluded as needed to a maximum of complete closure. In one embodiment of the present invention, the proximal end 61 of the accessory side arm 60 has two openings 88, 89 at a 90° angle to one another and each has a luer lock connection mechanism.

The distal sheath 40 has a proximal end and a distal end. The distal sheath 40 also includes a lumen 43 through which tools, instruments, stones and foreign bodies pass, an outer surface 44 and a lock 45 which is used to connect the proximal sheath 30 and the distal sheath 40 together and maintain the connection for as long as desired. Alternatively the distal sheath 40 and the proximal sheath 30 can be constructed as a single piece in a straight or in arm over sleeve type configuration. The distal sheath can be straight, tapered, expandable, or flared. The distal end of the distal sheath can be flat, beveled, convex, or concave. The preferred embodiment is a straight distal sheath with a flat end. The distal end may be coated with hydrophilic coating and/or polytetrafluoroethylene to reduce friction especially in a fluid environment. The distal sheath can be opaque, semi-transparent, transparent, or a combination of these. In the preferred embodiment, the distal sheath is opaque to avoid reflection of illuminating light of endoscope. The distal sheath may also have measurement markings to indicate the length of distal sheath has been advanced into the body cavity. The length of the distal sheath 40 may be in the range of 15 to 45 cm.

In one embodiment of the above method, the side arm 50 and/or the accessory side arm 60 emanate from the outer surface 34 of the proximal sheath 30 at an angle of between 20° and 80° toward the proximal end 31 of the sheath. In another embodiment, the above methods may further comprise the step of introducing a guide wire into a lumen or cavity of a patient's body containing one or more stones or foreign bodies prior to inserting the sheath 20 into a lumen or cavity of a patient's body in order to aid in the positioning the distal end 22 of the sheath in a position in close proximity to the stones or foreign bodies. In yet another embodiment, the above methods may further comprise the step of visualizing one or more stones and/or foreign objects which are too large to pass though the space between the scope and the inside surface of the sheath 20, but small enough to pass through the lumen 23 of the sheath, retracting the scope from the distal end 22 of the sheath to a point which is just proximal to the location within the proximal sheath 30 In yet another embodiment, the above method may further comprise the step of where the side arm 50 emanates from the proximal sheath while visualizing the aspiration of the one or more stones and/or foreign objects up the sheath and into the side arm and collecting the stone, foreign body and/or fragments in the collection container 80. In still another embodiment, the scope has a diameter which is smaller (at least 20% smaller) than an inner diameter of the sheath of the suction evacuation assembly resulting in an open channel within the lumen 23 of the sheath which permits the passage of stones, pieces of stones or other foreign objects through the lumen 23 of the sheath and through the one or more side arms (50, 53, 60, 63).

In one embodiment of the present invention, the above methods may further comprise the step of providing a sheath 20 that is comprised of a proximal sheath 30 and a distal sheath 40, the proximal sheath 30 having a proximal end 31 and a distal end 32 and the distal sheath 40 having a proximal end 41 and a distal end 42, wherein the distal end 32 of the proximal sheath is secured to the proximal end 41 of the distal sheath and wherein the proximal sheath 30 has a primary side arm 50 emanating from the outer surface 34 of the proximal sheath and a secondary (accessory) side arm 60 emanating from the outer surface 34 of the proximal sheath with the accessory side arm 60 providing an additional access point for irrigation, a catheter, a guide wire, a foreign body basket, a back stop, or other instrument or device to be passed through the sheath 20 anytime during the procedure to improve the efficacy of the procedure and the accessory will side arm 60 further comprising one or more sluices to allow the passage of any combination of the above mentioned instruments.

In another embodiment of the present invention, the above methods may further comprise the step of steps of introducing a guide wire into a lumen or cavity of a patient's body containing one or more stones or foreign bodies prior to inserting the sheath 20 into a lumen or cavity of a patient's body in order to aid in the positioning the distal end 22 of the sheath in a position in close proximity to the stones or foreign bodies, providing a secondary sheath 130 (See FIGS. 18 and 19) secured to the outer surface 24 of the sheath 20, now a primary sheath, passing the guide wire through the secondary sheath 130 while positioning the distal end 22 of the primary sheath in a position in close proximity to the stones or foreign bodies. In still another embodiment of the above methods, the secondary sheath 130 may be used to guide additional irrigation, a catheter, a foreign body basket, a backstop, an instrument or device to the position in close proximity to the stones or foreign bodies simultaneously with the scope and/or irrigation, catheter, foreign body basket, backstop, instrument or device through the primary sheath 20. In yet another embodiment of the above methods, the secondary sheath 130 has a proximal end 131 which is located near the proximal end 21 of the primary sheath and a distal end 132 which extends beyond the distal end 22 of the primary sheath in order to allow irrigation, a catheter, a foreign body basket, a backstop, an instrument or device to be passed beyond a stone, a stone fragment or other foreign body during a procedure to remove or perform Lithotripsy on them.

In yet another embodiment, the distal sheath 40 is formed by two concentric sheaths, one larger and one smaller. The lumen of the larger sheath is contiguous with the distal end 32 of the proximal sheath and the lumen 63 of the first side arm 50. The lumen 133 of the secondary sheath is smaller and is contiguous with the lumen 63 of the second side arm 60. In essence this configuration forms two separate chambers for the main tube. In still another embodiment, the distal end of the secondary sheath 130 (the smaller concentric tube) protrudes for some distance beyond the primary sheath 20 (the larger concentric tube). The distance is about 1 cm, 2 cm 3 cm or less than 5 cm. In yet another embodiment, the distal sheath 40 is made of more than two concentric tubes in various configurations. The proximal sheath 30 and distal sheath 40 may be constructed of the same or different materials and rigidity. In one embodiment of the present invention, the proximal sheath 30 is rigid and constructed of polypropylene, polycarbonate, or polyvinyl chloride while the distal sheath 40 is semi-rigid and is constructed of nylon, polyethylene, or fluorinated ethylene propylene.

Tables 1 through 5 below describe several embodiments for surgery instruments known in the art:

TABLE 1

Super-Mini Percutaneous Nephroscope Assembly

| Sheath Length: | Distal Length 13 CM plus 1 CM insertion Length Proximal Length 6.5 CM | |
|---|---|---|
| Sizes: | Range: | 3-8 mm |
| | 10 French (Fr.) | 3.3 mm |
| | 12 Fr., | 4.0 mm |
| | 14 Fr., | 4.7 mm |
| | 16 Fr., | 5.3 mm |
| | 18 Fr., | 6.0 mm |
| | 22 Fr. | 7.3 mm |

TABLE 2

Nephroscope Length: 26-33 CM

| Sizes: | 7.5 Fr. with Working Channel (2.5 mm) |
|---|---|
| | 9.0 Fr. with Working Channel (3.0 mm) |
| | 11.5 Fr. with Working Channel (3.85 mm) |

TABLE 3

Super-Mini Cysto-Ureteroscope Assembly

| Sheath Length: | For Bladder and Distal Ureter: Distal Length 18-24 (male-female) CM Mid Ureter: Distal Length 25 CM |
|---|---|
| Proximal Length | 6.5 CM |

TABLE 4

Cysto-Ureteroscope Length: 33 CM

| Sizes: | 7.5 Fr. with Working Channel (2.5 mm) |
|---|---|
| | 9.0 Fr. with Working Channel (3.0 mm) |
| | 11.5 Fr. with Working Channel (3.85 mm) |

TABLE 5

Ureteral Sheath:

| Distal Length: | 43.5 CM plus a 5 MM Insertion Length |
|---|---|
| | 38.5 CM plus a 5 MM Insertion Length |
| | 32.5 CM plus a 5 MM Insertion Length |
| | 26.5 CM plus a 5 MM Insertion Length |
| Proximal Length: | 5.5 CM |
| Sizes: | 12 Fr. ID (4.0 mm) and 14 Fr. OD (4.7 mm) |
| | 11.2 Fr. ID (3.7 mm) with 2.8 Fr. Coaxial Channel (1 mm) |
| | and 15 Fr. OD (5.0 mm) |

(ID—Inside Diameter/OD—Outside Diameter)

Obturator 90, as used herein, refers to an instrument which is known in the laparoscopic art. The obturator 90 is made of rigid, semi-rigid, or flexible material and may have a shaft 95 with an outer surface 94 which is either written or smooth in texture. It may have a solid or hollow center. The obturator 90 has a proximal end 91 and a distal end 92 which is inserted into the lumen 23, 33 sheath 24 proximal sheath 30. The distal end 92 may be straight, round, tapered, or beveled. The obturator 90 is to fit snuggly in the sheath 20. In one embodiment of the present invention, the obturator 90 has a hollow center creating a lumen 93 and a tapered distal end 92 and a guide wire may be passed through the lumen 93. In another embodiment, the obturator 90 is solid and the distal end 92 in beveled. The proximal end 91 of the obturator may be constructed as a handle for easy grasping and with a luer lock mechanism to allow for the attachment of an injection syringe. One embodiment may include a connection mechanism at distal end 92 of the obturator located at the interface between the obturator and the proximal end 21 of the sheath 20. In another embodiment the obturator 90 includes a male to female type screw on connector which allows the obturator 90 to be engaged to the proximal end of the proximal sheath after insertion into the proximal sheath after which the screw on connector may be disengaged and the obturator 90 withdrawn from the lumen 23 of the sheath. In still another embodiment the connection is made by twisting a luer lock mechanism of the obturator and the sheath. This will prevent the disengagement of the sheath from the obturator during the passage of the sheath through the body.

Flexible cap, as used herein, refers to a device which is constructed to fit the proximal end 21 of the sheath 20. The center opening may be self-sealing and the cap may be comprised of rubber, silicone, or any material known to be acceptable in the art.

Connecting tubing 70 is well known in the art. Connecting tubing 70 can be rigid, semi-rigid, or flexible tube of any medical grade material. Each piece of tubing as a proximal end 71 and a distal end 72, a lumen 73 through which material may travel and an outer surface. In one embodiment, the tubing is made of a clear PVC tubing. The tubing is used to connect a side arm 50, an accessory side arm 60, or any part thereof to either a collection container 80, a negative pressure system 120, or any other device known in the art. In one embodiment of the present invention, a primary tube 76 is connected by one end to a side arm 50 or an accessory side arm 60 and connected at the opposite end to an ingress opening 82 on a collection container 80 and a secondary tube 78 is connected by one end to an egress opening 83 on a collection container 80 and connected at the opposite end to a negative pressure system 120.

Figure 1:
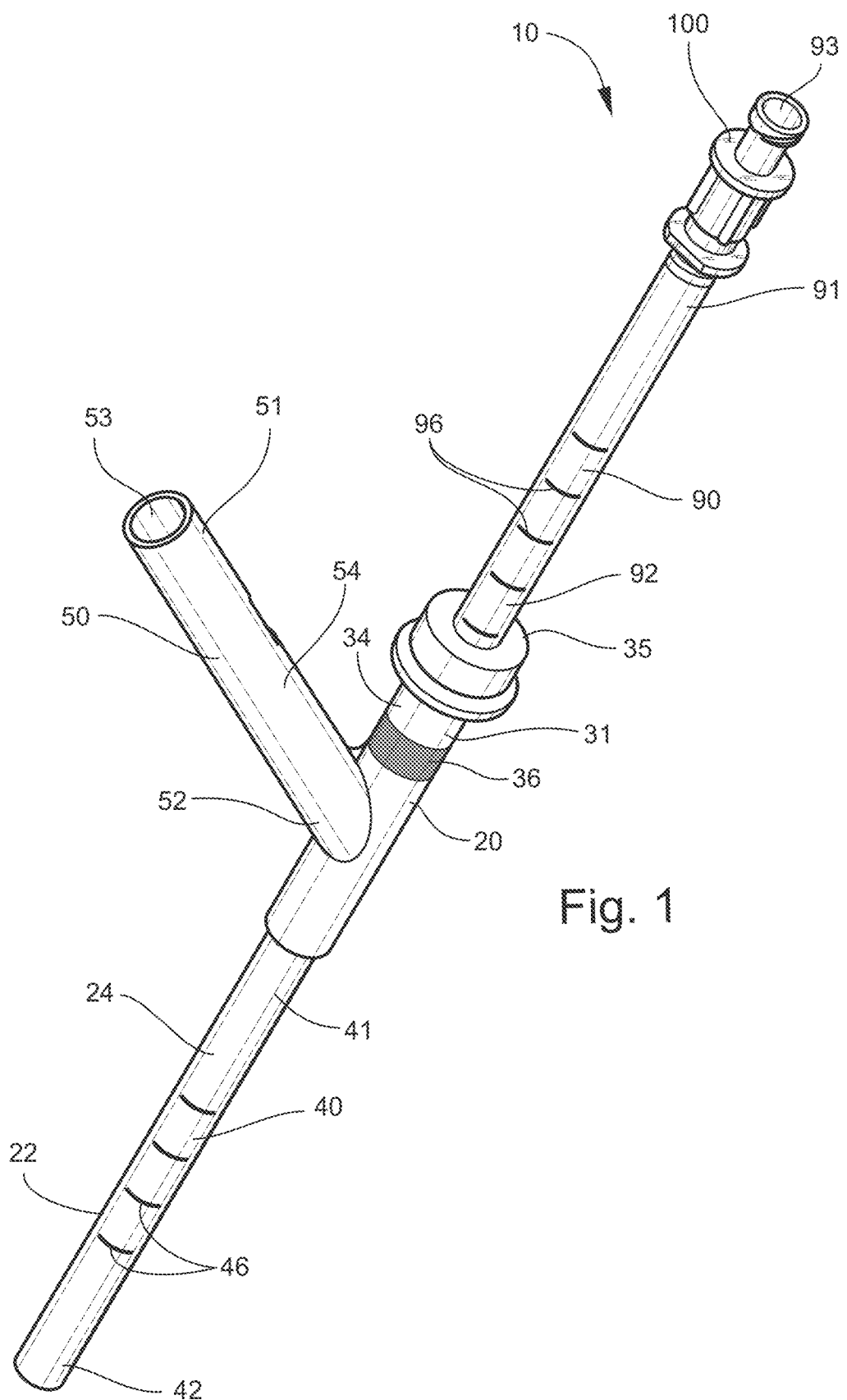
FIG. 1 is a perspective view of one embodiment of the present invention.
Figure 6:
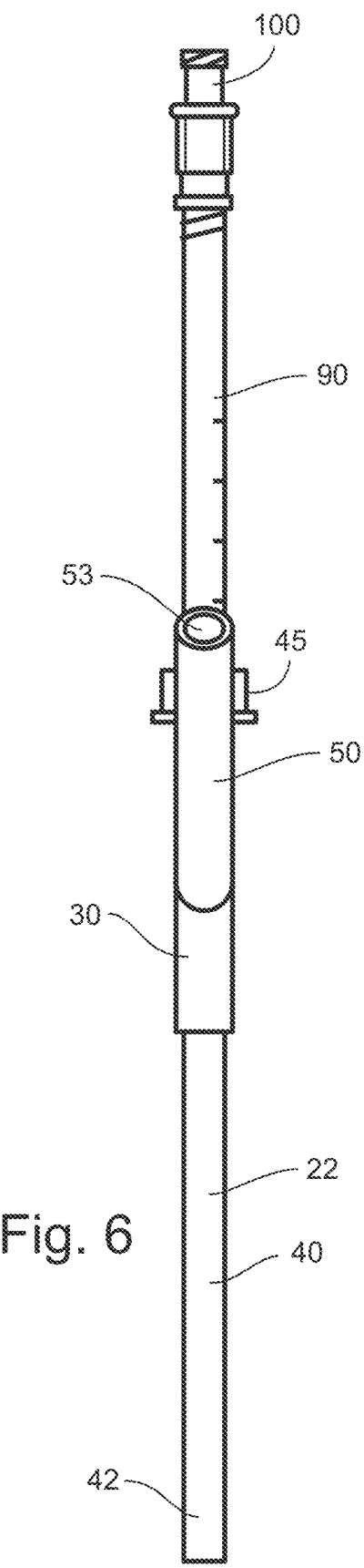
FIG. 6 is a side view of one embodiment of the present invention.
Figure 7:
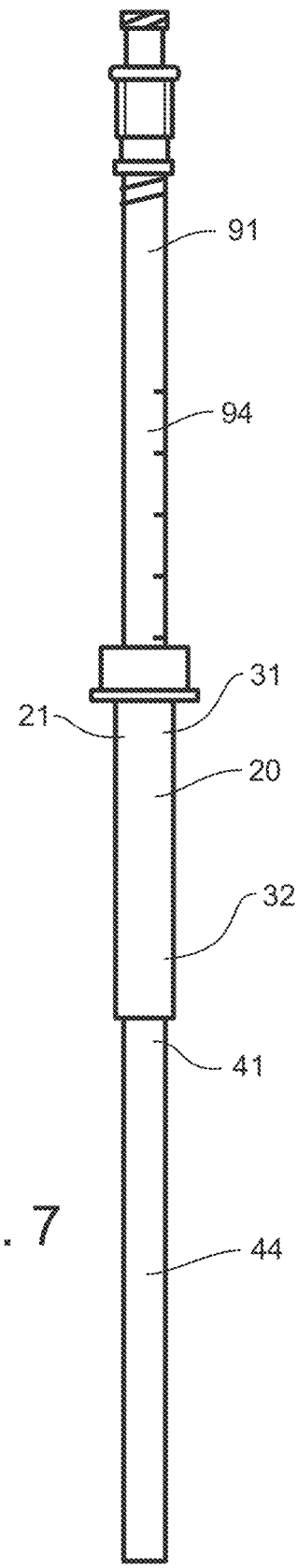
FIG. 7 is a side view of one embodiment of the present invention.
Figure 8:
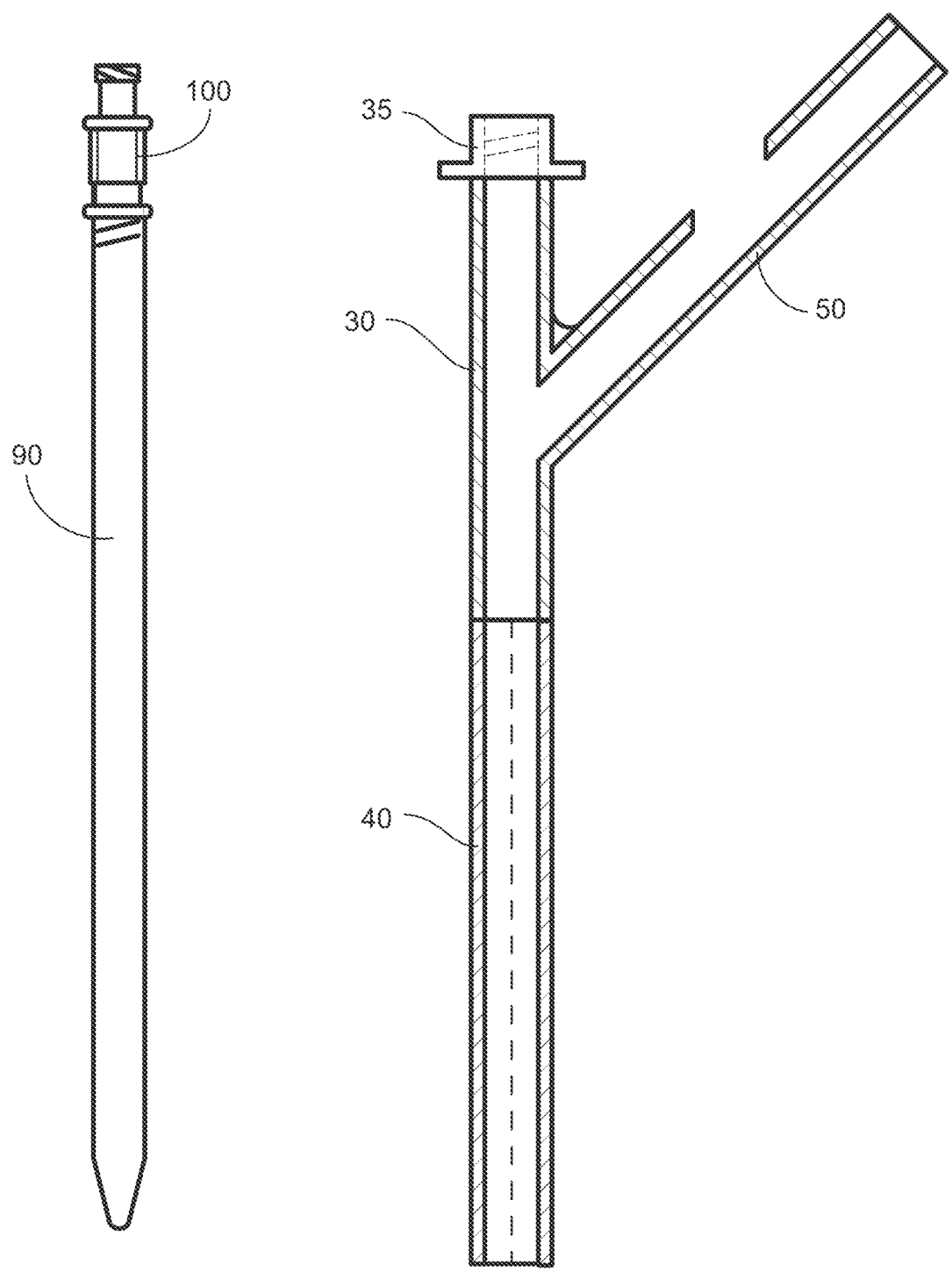
FIG. 8 is a cut-through view of one embodiment of the present invention.
Figure 9:
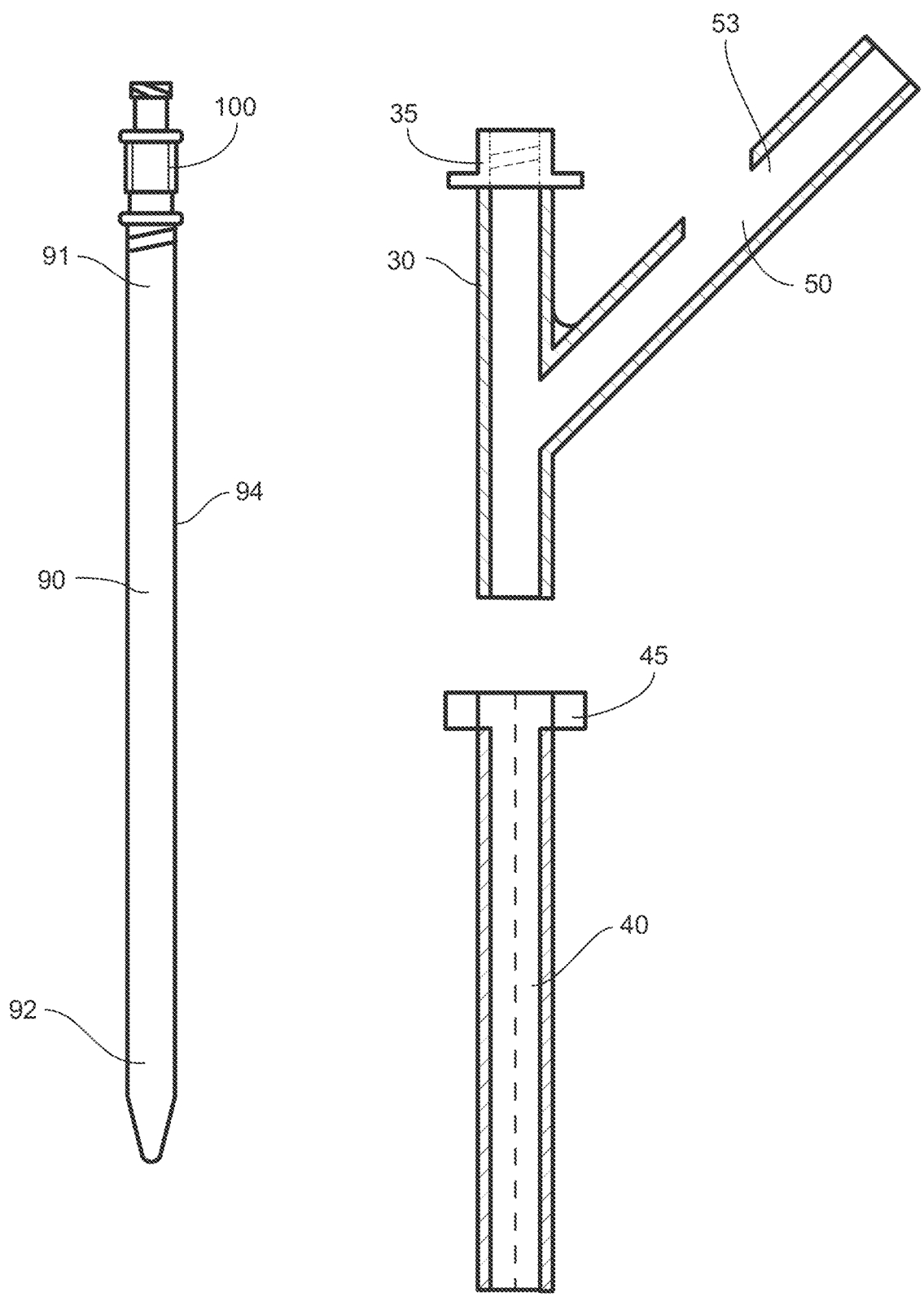
FIG. 9 is a cut-through view of one embodiment of the present invention.
Figure 10:
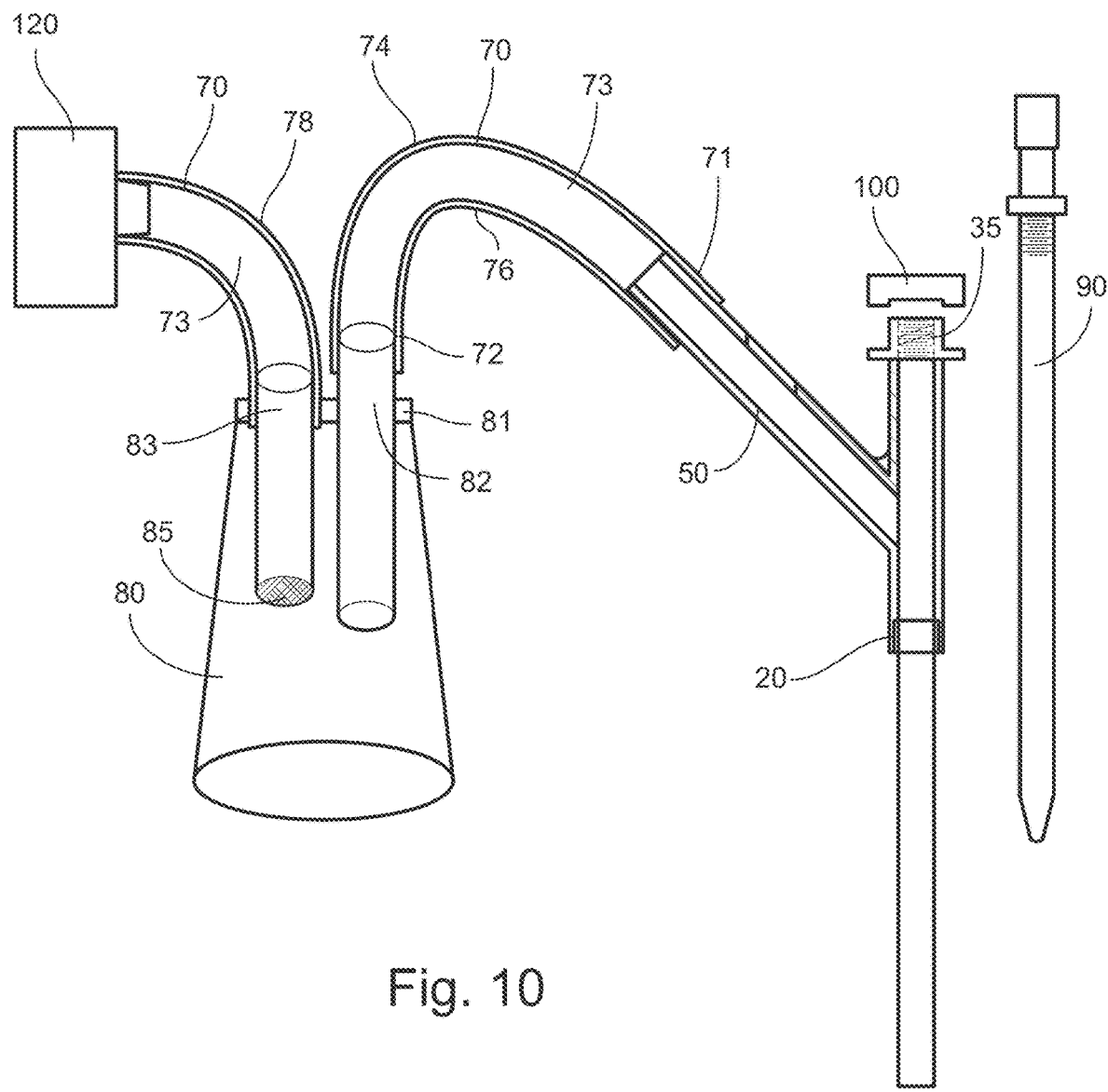
FIG. 10 is a cut-through view of one embodiment of the present invention.
Figure 11:
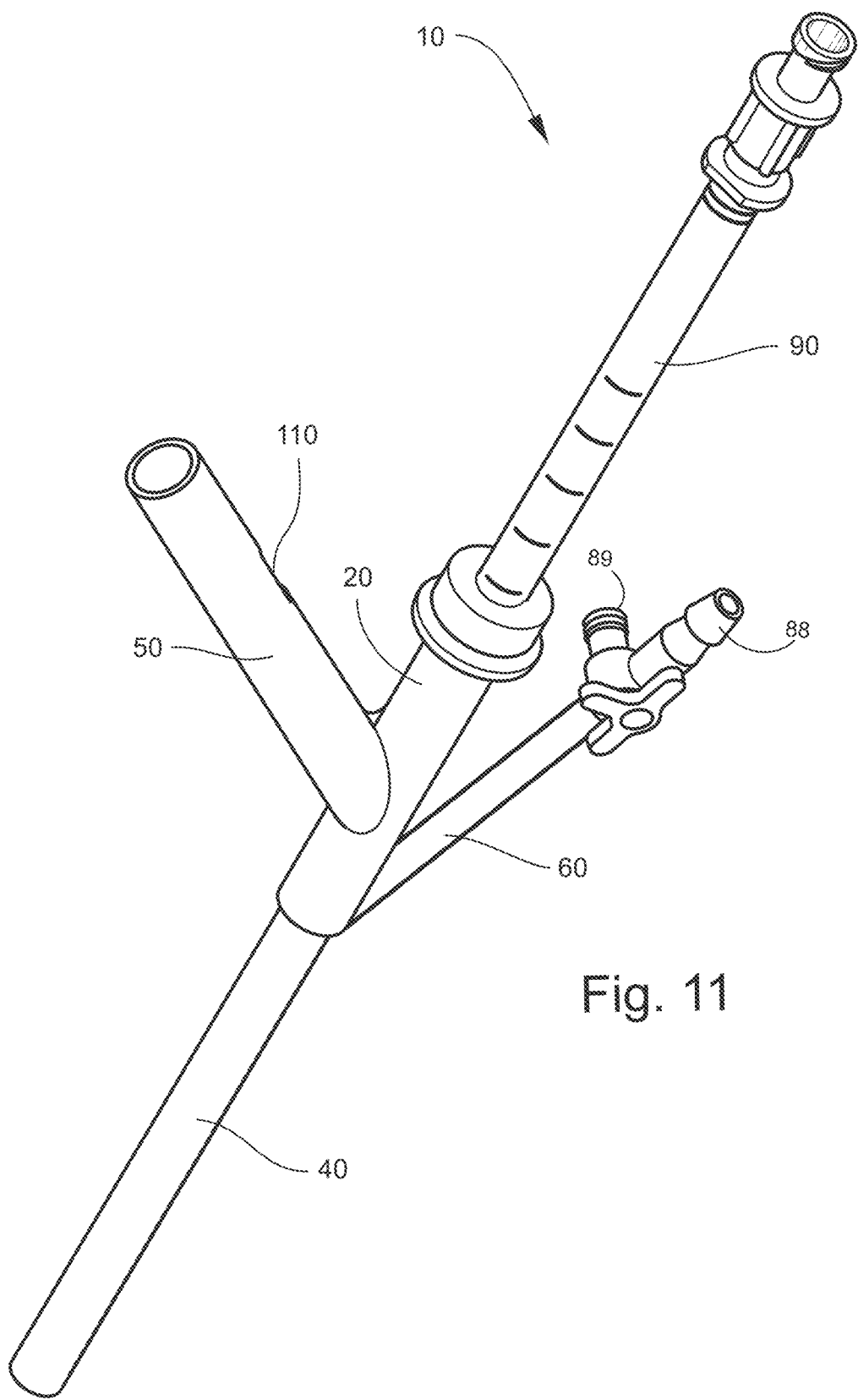
FIG. 11 is a perspective view of one embodiment of the present invention.
Figure 17:
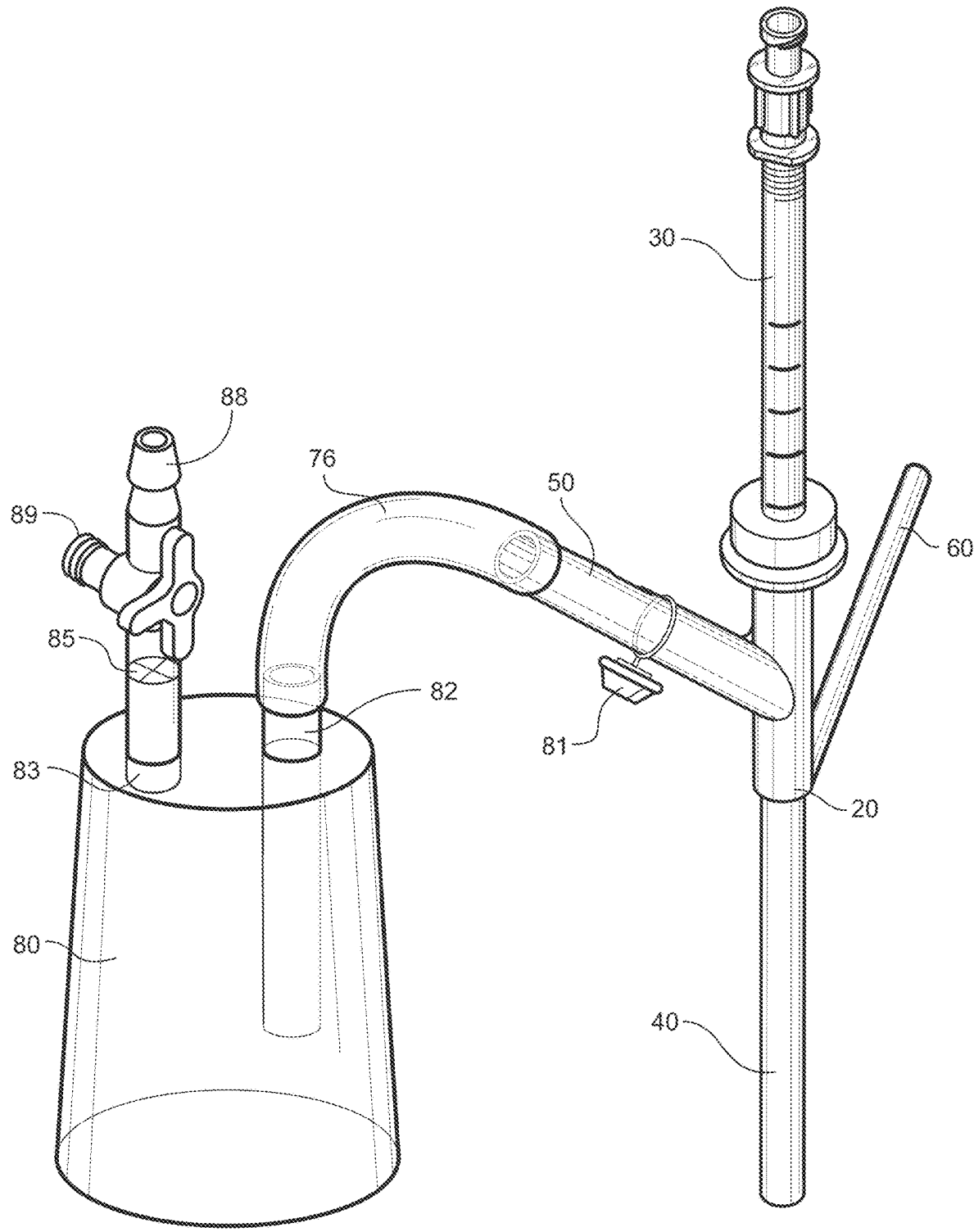
FIG. 17 is a perspective view of one embodiment of the present invention.

Collection container 80 is a container of any shape. It has a cap 81 and a bottom. The cap has an ingress (intake) opening 82 into and an egress (outflow) opening 83. The ingress opening 82 may or may not have a one way valve to prevent regurgitation of fluid and other materials into the connecting tubing 70. The egress opening 83 or anywhere along the egress tubing may be fitted with a sieve like mechanism to prevent the outflow of small stone or foreign body fragments or other materials from the collection container 80. The ingress opening has a connecting mechanism for connection to the connecting tubing 70. The egress channel has connecting mechanism to connect to a standard negative pressure aspiration machine. The bottom of the collection container 80 may contain a screw on or pull tab mechanism for the removal of specimen from the collection container 80. In one embodiment, the ingress tubing 82 is a longer, rigid tube which extends deeper into the collection container 80 while the egress tubing 83 is a shorter, rigid tube with a sieve 85 at the end that is inside the collection container. The bottom of the collection container has a pull tab for removal of collected specimens. In another embodiment, the egress tubing 83 is fitted with a side arm having a three-way valve 86 (FIGS. 10 and 17). The straight arm 88 is connected to the negative pressure system 120 while the right angle arm 89 is connected to a syringe. In normal operation the right angle side arm is closed. However, when there are stone fragments, blood clots, or tissue fragments obstructing the egress tubing 83, the right angle port can be opened to clear the obstructing objects by using irrigation with the attached syringe.

The instant invention also includes a device for removing a stone, a stone fragment, a foreign body, or tissue fragment from a patient comprising: a suction evacuation assembly 10 which includes a sheath 20 and one or more side arms 50, an obturator 90 which is inserted into a proximal end 21 of the sheath and which extends beyond the distal end 22 of the sheath and is releasably secured to the proximal end of the sheath, where the sheath is comprised of a proximal sheath 30 and a distal sheath 40, the proximal sheath 30 having a proximal end 31 and a distal end 32 and the distal sheath 40 having a proximal end 41 and a distal end 42 and wherein the distal end 32 of the proximal sheath is secured to the proximal end 41 of the distal sheath. A side arm 50 emanates from the outer surface 34 of the proximal sheath and an accessory side arm 60 emanates from the outer surface 34 of the proximal sheath where the proximal sheath 30 and the distal sheath 40 each have a lumen (33, 43 respectively) which is the same diameter as the lumen of the side arm 53 and as a lumen of the accessory side arm 63. A flexible cap 100 is releasably secured to the proximal end 21 of the sheath and a proximal end of a primary tube 71 is releasably secured to the proximal end 61 of the accessory side arm and the distal end of the primary tube is releasably secured to an ingress opening 82 of a collection container 80. A proximal end of a secondary tube 78 is releasably secured to the collection container 80 and a distal end of the secondary tube 78 is releasably secured to a negative pressure system 120 where the obturator 90 is withdrawn from the sheath 20 and a scope is inserted into the distal end 21 of the sheath through the flexible cap 100 and into the patient in order to visualize the stone or foreign body using the scope. The negative pressure system 120 is activated in order to remove the stone, foreign body, or tissue fragment from the cavity if a diameter of the stone, foreign body, or tissue fragment is narrower than an inside diameter of the sheath (lumen 23) and the side arm, or lithotripsy/ablation/morcellation is performed on the objects in order to create fragments with a decreased diameter which allow the passage of the fragments within the inside diameter of the sheath (lumen 23) and the lumen 53 of the side arm and/or accessory side arm 60. If the scope is withdrawn to the marking band 36, this would further open up the egress channel to allow unimpeded movement of the objects. The stone, foreign body and/or tissue fragments are collected in the collection container 80. Lithotripsy can be accomplished with any of the current available lithotripters: mechanical or electromechanical (the pneumatic lithotripter), electrohydraulic, ultrasonic, or laser. Tissue ablation can be accomplished with any currently available thermal energy device. Tissue morcellation is generally achieved with currently available mechanical morcellator.

In one embodiment of the above device, the side arm 50 and the accessory side arm 60 each emanate from the outer sheath 34 of the proximal sheath at an angle of between 20° and 80° toward the proximal end 31 of the sheath. In another embodiment, a guide wire which is introduced into a lumen or cavity of a patient's body containing one or more stones, foreign bodies or targeted tissue/organ prior to inserting the sheath 20, 40 into a lumen or cavity of a patient's body in order to aid in the positioning the distal end 22, 42 of the sheath in a position in close proximity to the stones or foreign bodies. In still another embodiment, the side arm 50 and the accessory side arm 60 each further comprises a pressure regulating mechanism which allows a person using the suction evacuation assembly 10 to increase or decrease the negative pressure within the suction evacuation assembly. In yet another embodiment the scope has a diameter which is smaller than an inner diameter of the sheath 20, 30, 40 of the suction evacuation assembly 10 resulting in an open channel within the lumen 23, 33, 43 of the sheath which permits the passage of stones, pieces of stones or other foreign objects through the lumen of the sheath and through the side arm 50 and/or accessory side arm 60.

In one embodiment of the present invention, the suction evacuation assembly 10 further comprises a secondary sheath 130 secured to the outer surface 24 of the sheath, now a primary sheath. The secondary sheath 130 allows the passage of a guide wire through the lumen 133 of the secondary sheath while positioning the distal end 22 of the primary sheath in a position in close proximity to the stones or foreign bodies. In another embodiment, the secondary sheath 130 may be used to guide additional irrigation, a catheter, a foreign body basket, a backstop, an instrument or device to the position in close proximity to the stones or foreign bodies simultaneously with the scope and/or irrigation, catheter, foreign body basket, backstop, instrument or device through the primary sheath. In yet another embodiment, the secondary sheath 130 has a proximal end 131 which is located near the proximal end 21 of the primary sheath and a distal end 132 which extends beyond the distal end 22 of the primary sheath in order to allow irrigation, a catheter, a foreign body basket, a backstop, an instrument or device to be passed beyond a stone, a stone fragment or other foreign body during a procedure to remove them.

The suction evacuation assembly 10 may include a flexible cap 100 which is designed to engage an actuation device. An actuation device may include a handle and an actuator which is engaged with a cable. The cable then passes through the flexible cap 100 and is then slidably disposed within the lumen 23 of a sheath. In one embodiment of the present invention, a wire basket retriever is located on the distal end of a cable. The proximal end of the cable is releasably engaged to an actuator within the handle of an actuation device. The actuation device may include any device known in the art. An operator may hold the handle and operate the actuator in a slidable manner moving the actuator in a proximal and distal direction relative to the flexible cap 100.

The suction evacuation assembly 10 may also include additional tools and attachments which aid in the extraction of one or more stones or other foreign bodies from a patient. Each of the tools mentioned herein may be inserted into the proximal end of a sheath 20, side arm 54 or accessory side arm 60 and fed into the lumen 23, 43 or 53 in a slideable manner until reaching the distal end 22 of the sheath. The tools may then be locked in place, actuated with the aid of an actuation device, manipulated by an individual (i.e. a physician, nurse, surgical technician, etc.), or utilized in any manner known in the art.

In one embodiment of the present invention, the suction evacuation assembly 10 may further include a wire basket retriever (not illustrated) which is used to collect and extract stones from a patient. The wire basket retriever may be made up of two or more wires which allow the wire basket to envelop an object (i.e. a stone) to either hold it in place or extract it.

In yet another embodiment, the suction evacuation assembly 10 may further include a loop 100 (not illustrated) to aid in the removal of stones or other undesirable materials or tissues. The loop may be electrified to permit the cautery removal of tissues such as polyps (i.e. a polypectomy loop). A loop may be either permanently or temporarily attached to a cable which may be either permanently or temporarily attached to either a flexible cap 100 which may be engaged to the distal end of a side arm 50 or accessory side arm 60. In still another embodiment, the suction evacuation assembly 10 may further include a grasping tool (not illustrated) which would enable the user (i.e. a surgeon) to grasp and manipulate objects and/or tissues. In another embodiment of the present invention, all parts of the suction evacuation assembly 10 in all tools and instruments associated with it are autoclaveable.

In one embodiment of the present invention the device can also be used for tissue ablation.

Methodology: The distal sheath 40 is advanced to the target organ either under direct vision or through ultrasonic/radiological guidance with or without guide wire. An endoscope with tissue ablation instrument is passed through the sheath 40. Tissue is ablated or morcellated, tissue fragments are evacuated between the space of the scope and the sheath or alternatively if the tissue fragments are too large to be evacuated from this space but small enough to enter the sheath, the scope can be withdrawn to the bifurcation to allow unimpeded passage of the tissue. The accessory channel or channels can be used for additional irrigation, passage of guide wire, grasper, or any other devices or instruments. With the expandable distal sheath 40, the sheath can be advanced while dilating the space/lumen. In addition and/or alternatively, the expanded distal end 42 can be used to entrap the objective inside the shaft to perform fragmentation, ablation, morcellation, or extraction.

1. A method for removing a stone, a stone fragment or a foreign body from a patient using a suction evacuation assembly comprising the steps of:
   providing a suction evacuation assembly which includes a sheath and one or more side arms;
   inserting an obturator into a proximal end of a sheath and securing said obturator to the proximal end of said sheath;
   said sheath being comprised of a proximal sheath and a distal sheath, said proximal sheath having a proximal end and a distal end and said distal sheath having a proximal end and a distal end;
     wherein the distal end of said proximal sheath is secured to the proximal end of said distal sheath and wherein said proximal sheath has one or more side arms emanating from the outer surface of said proximal sheath; and
     wherein the sheath having a lumen which is the same diameter as a lumen of said one or more side arms;
   inserting a distal end of said sheath into a lumen or cavity of a patient's body containing one or more stones or foreign bodies;
   positioning the distal end of said sheath in a position in close proximity to said stones or foreign bodies;
   disengaging said obturator from the proximal end of said sheath and removing said obturator from said sheath;
   securing a flexible cap to the proximal end of the sheath;
   connecting one end of a primary tube to one of the side arms and connecting the other end of said primary tube to a collection bottle;
   connecting one end of a secondary tube to said collection bottle and connecting the other end of said secondary tube to a negative pressure system;
   inserting a scope into the sheath through the flexible cap and into said patient;
   visualizing said stone or foreign body using said scope;
   activating said negative pressure system in order to remove said stone or foreign body from said cavity if a diameter of said stone or foreign body is narrower than an inside diameter of said sheath and said side arm, or performing a lithotripsy on said stone or said foreign body in order to create fragments with a decreased diameter which allow the passage of said fragments within the inside diameter of said sheath and said side arm; and collecting the stone, foreign body and/or fragments in said collection bottle.

2. The method of claim 1 wherein said one or more side arms emanate from the outer surface of said proximal sheath at an angle of between 20° and 80° toward the proximal end of said sheath.

3. The method of claim 1 further comprising the step of:
introducing a guide wire into a lumen or cavity of a patient's body containing one or more stones or foreign bodies prior to inserting said sheath into a lumen or cavity of a patient's body in order to aid in the positioning the distal end of said sheath in a position in close proximity to said stones or foreign bodies.

4. The method of claim 1 further comprising the step of:
visualizing one or more stones and/or foreign objects which are too large to pass though the space between the scope and the inside surface of the sheath, but small enough to pass through the lumen of the sheath;

retracting the scope from the distal end of the sheath to a point which is just proximal to the location within the proximal sheath where said side arm emanates from said proximal sheath while visualizing the aspiration of said one or more stones and/or foreign objects up the sheath and into said side arm; and collecting the stone, foreign body and/or fragments in said collection container.

5. The method of claim 1 further comprising the steps of:
providing a sheath that is comprised of a proximal sheath and a distal sheath, said proximal sheath having a proximal end and a distal end and said distal sheath having a proximal end and a distal end;

wherein the distal end of said proximal sheath is secured to the proximal end of said distal sheath and wherein said proximal sheath has a primary side arm emanating from the outer surface of said proximal sheath and a secondary side arm emanating from the outer surface of said proximal sheath;

said second side arm providing an additional access point for irrigation, a catheter, a guide wire, a foreign body basket, a back stop, or other instrument or device to be passed through the sheath anytime during the procedure to improve the efficacy of the procedure; and said second side arm further comprising one or more sluices to allow the passage of any combination of the above mentioned instruments.

6. The method of claim 1 wherein said one or more side arms further comprises a pressure regulating mechanism which allows a person using the suction evacuation assembly to increase or decrease the negative pressure within the suction evacuation assembly.

7. The method of claim 1 wherein the scope has a diameter which is smaller than an inner diameter of the sheath of the suction evacuation assembly resulting in an open channel within the lumen of the sheath which permits the passage of stones, pieces of stones or other foreign objects through the lumen of the sheath and through said one or more side arms.

8. The method of claim 1 further comprising the steps of:
introducing a guide wire into a lumen or cavity of a patient's body containing one or more stones or foreign bodies prior to inserting said sheath into a lumen or cavity of a patient's body in order to aid in the positioning the distal end of said sheath in a position in close proximity to said stones or foreign bodies;

providing a secondary sheath secured to the outer surface of the sheath, now a primary sheath;

passing the guide wire through the secondary sheath while positioning the distal end of said primary sheath in a position in close proximity to said stones or foreign bodies.

9. The method of claim 8 wherein said secondary sheath may be used to guide additional irrigation, a catheter, a foreign body basket, a backstop, an instrument or device to the position in close proximity to said stones or foreign bodies simultaneously with the scope and/or irrigation, catheter, foreign body basket, backstop, instrument or device through the primary sheath.

10. The method of claim 9 wherein said secondary sheath has a proximal end which is located near the proximal end of the primary sheath and a distal end which extends beyond the distal end of the primary sheath in order to allow irrigation, a catheter, a foreign body basket, a backstop, an instrument or device to be passed beyond a stone, a stone fragment or other foreign body during a procedure to remove them.

11. The method of claim 1 wherein, the method could also be used for tissue ablation and morcellation 12. A device for removing a stone, a stone fragment or a foreign body from a patient comprising:
a suction evacuation assembly which includes a sheath and one or more side arms;

an obturator which is inserted into a proximal end of the sheath and which extends beyond the distal end of the sheath and releaseably secured to the proximal end of said sheath;

said sheath being comprised of a proximal sheath and a distal sheath, said proximal sheath having a proximal end and a distal end and said distal sheath having a proximal end and a distal end;

wherein the distal end of said proximal sheath is secured to the proximal end of said distal sheath;

a side arm emanating from the outer surface of said proximal sheath;

a accessory side arm emanating from the outer surface of said proximal sheath;

said sheath having a lumen which is the same diameter as a lumen of said side arm and as a lumen of said accessory side arm;

a flexible cap releaseably secured to the proximal end of the sheath;

a proximal end of a primary tube releaseably secured to said accessory side arm and a distal end of said primary tube releaseably secured to a collection container; and a proximal end of a secondary tube releaseably secured to said collection container and a distal end of said secondary tube releaseably secured to a negative pressure system;

wherein said obturator is withdrawn from said sheath and a scope is inserted into the sheath through the flexible cap and into said patient in order to visualize said stone or foreign body using said scope;

the negative pressure system is activated in order to remove said stone or foreign body from said cavity if a diameter of said stone or foreign body is narrower than an inside diameter of said sheath and said side arm, or lithotripsy is performed on said stone or said foreign body in order to create fragments with a decreased diameter which allow the passage of said fragments within the inside diameter of said sheath and said side arm; and the stone, foreign body and/or fragments are collected in said collection container.

13. The device of claim 12 wherein said side arm and said accessory side arm each emanate from the outer sheath of said proximal sheath at an angle of between 20° and 80° toward the proximal end of said sheath.

14. The device of claim 12 further comprising:
a guide wire which is introduced into a lumen or cavity of a patient's body containing one or more stones or foreign bodies prior to inserting said sheath into a lumen or cavity of a patient's body in order to aid in the positioning the distal end of said sheath in a position in close proximity to said stones or foreign bodies.

15. The device of claim 12 wherein said side arm and said accessory side arm each further comprise a pressure regulating mechanism which allows a person using the suction evacuation assembly to increase or decrease the negative pressure within the suction evacuation assembly.

16. The device of claim 12 wherein the scope has a diameter which is smaller than an inner diameter of the sheath of the suction evacuation assembly resulting in an open channel within the lumen of the sheath which permits the passage of stones, pieces of stones or other foreign objects through the lumen of the sheath and through said side arm and/or accessory side arm.

17. The device of claim 12 wherein the suction evacuation assembly further comprising:
a secondary sheath secured to the outer surface of the sheath, now a primary sheath;
said secondary sheath allows the passage of a guide wire through the secondary sheath while positioning the distal end of said primary sheath in a position in close proximity to said stones or foreign bodies.

18. The device of claim 17 wherein said secondary sheath may be used to guide additional irrigation, a catheter, a foreign body basket, a backstop, an instrument or device to the position in close proximity to said stones or foreign bodies simultaneously with the scope and/or irrigation, catheter, foreign body basket, backstop, instrument or device through the primary sheath.

19. The device of claim 18 wherein said secondary sheath has a proximal end which is located near the proximal end of the primary sheath and a distal end which extends beyond the distal end of the primary sheath in order to allow irrigation, a catheter, a foreign body basket, a backstop, an instrument or device to be passed beyond a stone, a stone fragment or other foreign body during a procedure to remove them.

20. The device of claim 12 wherein the device is used for tissue ablation and morcellation.

The present invention may be embodied in other forms without departing from the spirit and the essential attributes thereof, and, accordingly, reference should be made to the appended claims, rather than to the foregoing specification, as indicating the scope of the invention. The invention illustratively discloses herein suitably may be practiced in the absence of any element which is not specifically disclosed herein.

I claim:

1. A device for removing a stone, a stone fragment or a foreign body from a patient comprising:
a suction evacuation assembly which includes a sheath and at least one side arm;
an obturator having a straight or tapered distal end which is inserted into a proximal end of the sheath and which extends beyond a distal end of the sheath and is releasably secured to the proximal end of said sheath;
the side arm emanating from an outer surface of said sheath, wherein said side arm further comprises a pressure regulating mechanism consisting of a longitudinal slit in respect of an axis of the side arm, accessible from an surface of said side arm, extending through said side arm, and having a depth equal to the thickness of a wall of the side arm, which allows a person using the suction evacuation assembly to increase the negative pressure within the suction evacuation assembly by covering the pressure regulating mechanism or decrease the negative pressure within the suction evacuation assembly by uncovering the pressure regulating mechanism;
a flexible cap releasably secured to the proximal end of the sheath;
a proximal end of a primary tube releasably secured to said side arm and a distal end of said primary tube releasably secured to a collection container; and
a proximal end of a secondary tube releasably secured to said collection container and a distal end of said secondary tube releasably secured to a negative pressure system;
wherein said obturator can be withdrawn from said sheath and a scope can be inserted into the sheath through the flexible cap and into said patient in order to visualize said stone or foreign body using said scope; and
wherein the negative pressure system can be activated in order to remove said stone or foreign body from a body cavity if a diameter of said stone or foreign body is narrower than an inside diameter of said sheath and said side arm, or lithotripsy can be performed on said stone or said foreign body in order to create fragments with a decreased diameter which allow the passage of said fragments within the inside diameter of said sheath and said side arm; and the stone, foreign body and/or fragments can be collected in said collection container.

2. The device of claim 1 further comprising:
a flexible, deflectable tip secured to the distal end of the sheath which will enable the user to adjust the direction of suction, irrigation, instrument placement, or removal of a stone, stone fragment or any other foreign body or tissue from a patient; and
an expandable distal end of the sheath, such as a balloon that can be inflated to hold the sheath in place within the body cavity.

3. The device of claim 1 further comprising an accessory side arm wherein said accessory side arm further comprises a second pressure regulating mechanism which allows a person using the suction evacuation assembly to increase or decrease the negative pressure within the suction evacuation assembly.

4. The device of claim 1 wherein the scope has a diameter which is smaller than an inner diameter of the sheath of the suction evacuation assembly resulting in an open channel within a lumen of the sheath which permits the passage of stones, pieces of stones or other foreign objects through the lumen of the sheath and through said side arm.

5. The device of claim 1 wherein the suction evacuation assembly further comprises:
   a secondary sheath secured to the outer surface of the sheath, now a primary sheath;
      said secondary sheath allows the passage of a guide wire through the secondary sheath while positioning the distal end of said primary sheath in a position in close proximity to said stones or foreign bodies.

6. The device of claim 5 wherein said secondary sheath may be used to guide additional irrigation, a catheter, a foreign body basket, a backstop, an instrument or device to the position in close proximity to said stones or foreign bodies simultaneously with the scope and/or irrigation, catheter, foreign body basket, backstop, instrument or device through the primary sheath.

7. The device of claim 6 wherein said secondary sheath has a proximal end which is located near the proximal end of the primary sheath and a distal end which extends beyond the distal end of the primary sheath in order to allow irrigation, a catheter, a foreign body basket, a backstop, an instrument or device to be passed beyond a stone, a stone fragment or other foreign body during a procedure to remove them.

8. A device for removing a stone, a stone fragment or a foreign body from a patient comprising:
   a suction evacuation assembly which includes a sheath and at least one side arm;
   an obturator having a straight or tapered distal end which is inserted into a proximal end of the sheath and which extends beyond a distal end of the sheath and is releasably secured to the proximal end of said sheath; said sheath having a proximal end and a distal end;
   the side arm emanating from an outer surface of said sheath, wherein said side arm further comprises a pressure regulating mechanism comprising a longitudinal slit in respect of an axis of the side arm, accessible from an outer surface of said side arm, extending through said side arm, and having a depth equal to the thickness of a wall of the side arm, which allows a person using the suction evacuation assembly to increase the negative pressure within the suction evacuation assembly by covering the pressure regulating mechanism or decrease the negative pressure within the suction evacuation assembly by uncovering the pressure regulating mechanism;
   a flexible cap releasably secured to the proximal end of the sheath;
   a proximal end of a primary tube releasably secured to said side arm and a distal end of said primary tube releasably secured to a collection container; and
   a proximal end of a secondary tube releasably secured to said collection container and a distal end of said secondary tube releasably secured to a negative pressure system;
      wherein said obturator can be withdrawn from said sheath and a scope can be inserted into the sheath through the flexible cap and into said patient in order to visualize said stone or foreign body using said scope; and
      wherein the negative pressure system can be activated in order to remove said stone or foreign body from said a body cavity if a diameter of said stone or foreign body is narrower than an inside diameter of said sheath and said side arm, or lithotripsy can be performed on said stone or said foreign body in order to create fragments with a decreased diameter which allow the passage of said fragments within the inside diameter of said sheath and said side arm; and
   the stone, foreign body and/or fragments can be collected in said collection container.

9. The device of claim 8 further comprising:
   a flexible, deflectable tip secured to the distal end of the distal sheath which will enable the user to adjust the direction of suction, irrigation, instrument placement, or removal of a stone, stone fragment or any other foreign body or tissue from a patient; and
   an expandable distal end of the sheath, such as a balloon that can be inflated to hold the sheath in place within the body cavity.

10. The device of claim 8 wherein the scope has a diameter which is smaller than an inner diameter of the sheath of the suction evacuation assembly resulting in an open channel within a lumen of the sheath which permits the passage of stones, pieces of stones or other foreign objects through the lumen of the sheath and through said side.

11. The device of claim 8 wherein the suction evacuation assembly further comprises:
   a secondary sheath secured to the outer surface of the sheath, now a primary sheath;
      said secondary sheath allows the passage of a guide wire through the secondary sheath while positioning the distal end of said primary sheath in a position in close proximity to said stones or foreign bodies.

12. The device of claim 11 wherein said secondary sheath may be used to guide additional irrigation, a catheter, a foreign body basket, a backstop, an instrument or device to the position in close proximity to said stones or foreign bodies simultaneously with the scope and/or irrigation, catheter, foreign body basket, backstop, instrument or device through the primary sheath.

13. The device of claim 12 wherein said secondary sheath has a proximal end which is located near the proximal end of the primary sheath and a distal end which extends beyond the distal end of the primary sheath in order to allow irrigation, a catheter, a foreign body basket, a backstop, an instrument or device to be passed beyond a stone, a stone fragment or other foreign body during a procedure to remove them.

* * * * *